(12) United States Patent
Hanke

(10) Patent No.: US 6,177,097 B1
(45) Date of Patent: Jan. 23, 2001

(54) SOLID ORAL ANTICARIOGENIC COMPOSITION FOR CLEANING THE ORAL CAVITY AND THE TEETH, AND A PROCESS FOR PRODUCING SAME

(75) Inventor: Günther Hanke, Flein (DE)

(73) Assignee: Einhorn Apotheke, Heilbronn (DE)

( * ) Notice: Under 35 U.S.C. 154(b), the term of this patent shall be extended for 0 days.

(21) Appl. No.: 09/147,547

(22) PCT Filed: Jul. 19, 1997

(86) PCT No.: PCT/EP97/03204

§ 371 Date: Jan. 19, 1999

§ 102(e) Date: Jan. 19, 1999

(87) PCT Pub. No.: WO98/03151

PCT Pub. Date: Jan. 29, 1998

(30) Foreign Application Priority Data

Jul. 19, 1996 (DE) ............................................. 196 29 167

(51) Int. Cl.[7] ............................... A61K 9/20; A61K 9/28; A61K 47/26
(52) U.S. Cl. ............................................ 424/440; 424/435
(58) Field of Search .................................... 424/435, 440

(56) References Cited

U.S. PATENT DOCUMENTS

| | | | |
|---|---|---|---|
| 3,525,791 | * 8/1970 | Ahrens | 424/280 |
| 3,911,099 | 10/1975 | DeFoney et al. | 424/28 |
| 4,157,386 | * 6/1979 | La Rochelle | 424/48 |
| 4,170,633 | 10/1979 | Wagenknecht | 424/48 |
| 4,587,119 | * 5/1986 | Bucke et al. | 424/48 |
| 4,620,982 | * 11/1986 | Serpelloni | 426/658 |
| 4,814,163 | * 3/1989 | Barth | 424/49 |
| 4,814,164 | * 3/1989 | Barth et al. | 424/49 |
| 4,971,708 | * 11/1990 | Cola et al. | 424/440 |
| 4,971,798 | 11/1990 | Coia et al. | 424/440 |
| 5,151,274 | * 9/1992 | Saltman et al. | 424/630 |
| 5,292,518 | * 3/1994 | Kuhrts | 424/439 |
| 5,496,541 | * 3/1996 | Cutler | 424/48 |
| 5,879,698 | * 3/1999 | Ellenbogon et al. | 424/440 |

FOREIGN PATENT DOCUMENTS

| | | | |
|---|---|---|---|
| 0 354 442 A1 | 2/1990 | (EP) | A23J/7/00 |
| 94/00101 | * 1/1994 | (WO) | . |
| 97/04741 | * 3/1997 | (WO) | . |
| 98/03151 | * 1/1998 | (WO) | . |

OTHER PUBLICATIONS

Nilner et al Acta Odontol Scand 49:267–272 Sugar Free Lozenger Sod. Polyphosphat 1.2% disodient Cited on pp. 2–3 of Hurmeilel 97/0474/(above) Phobat 3.3% Sodbicat 3.0% 42% Socbts, 1991.*

Willibald–Ettle Pharm Ind 58(10):947–952 ISSN 0031–711 X Isomalt Lozenge Xylitol, 1996.*

Tenovuo et al J. Oral. Rehabil 24(5):325–331 Calcium Phosphate Disodium Hydrogen Phosphate ISSN 0305–182X Magnesium Stearate Lozenge Cal. Carbonate Xylitol, 1997.*

* cited by examiner

Primary Examiner—Shep K. Rose
(74) Attorney, Agent, or Firm—Jacobson, Price, Holman & Stern, PLLC

(57) ABSTRACT

The present invention relates to a solid oral anticariogenic composition in the form of a sucking tablet for cleaning the oral cavity and the teeth, and to a process for producing such composition.

19 Claims, No Drawings

SOLID ORAL ANTICARIOGENIC COMPOSITION FOR CLEANING THE ORAL CAVITY AND THE TEETH, AND A PROCESS FOR PRODUCING SAME

The present invention relates to a solid oral anticariogenic composition in the form of a sucking tablet for cleaning the oral cavity and the teeth, and to a process for producing such composition.

It is generally known that carbohydrates, such as sugars, present in the dental plaque after the consumption of foods, especially sweets, are converted to acids which again cause dental caries.

Sugars, in particular white refined sugar (saccharose), cause and promote caries, especially when often consumed between the meals. The acids formed from sugars in the dental plaque, such as ketoses, aldoses, hexoses etc., are further known to demineralize the dental surface and to produce cavities. In the dental plaque, the acids are formed within a few minutes after the consumption of sugar-containing foods. After five minutes of saccharose action, the acidity of the dental plaque is a hundred times higher than that recorded before such action.

From the prior art, alkaline compounds, such as sodium hydrogencarbonate, sodium carbonate, ammonium phosphate and others, are known for the neutralization of acids in the dental plaque.

A disadvantage of those alkaline buffers is their salty taste which greatly reduces their acceptance by the consumer.

Further, R. Clark, D. I. Hay et al., Brit. D. J. 111: 244 (1961), and B. T. Gilders, Brit. D. J. 110: 17 (1961), recommend the use of acidic "tooth cleaning tablets" which induce an intensive flow of natural saliva. However, a drawback of this tablet was the lack of neutralization of the dental plaque.

Among the more recent prior art references, EP-B-0 486 563 describes a chewing gum composition which releases active substances in an accelerated and controlled way. The active substances include dietetic supplements, antiseptic agents, antismoking agents, artificial sweeteners, flavors and curatives. Resin components, such as terpene resin, gum rosin or glycerol esters of partially hydrogenated wood, are used as the carrier. Polyoxyethylene sorbitol fatty acid esters, polyglycerol esters and sorbitol esters of fatty acids, for example, serve as solubilizers.

WO 92/02149 describes low-calorie moisture-resistant chewing compositions consisting of polydextrose and isomalt or mannitol, and processes for producing same.

DE-42 21 054 describes a preparation for the prophylactic and therapeutic treatment of caries, characterized in that substances containing calcium and phosphate are added to the base consisting of sugar or sugar substitutes, and a process for producing such preparation.

EP-B-0 222 846 describes a solid oral anticariogenic composition in the form of a chewing gum or a pastille for the neutralization of acids in dental plaques. In addition to sorbitol as a carrier and other conventional ingredients, the gums and pastilles contain urea in an amount of from 0.05 to 80% by weight. Since sorbitol has a slightly cariogenic activity, urea is added which is known to inhibit the acid formation.

However, it is also known that the acid binding property of urea is not very pronounced. Another disadvantage of urea is the fact that it is not subject to evaluation under food law.

Thus, it has been the object of the invention to provide a solid oral anticariogenic composition for cleaning the oral cavity and the teeth which lacks the above mentioned drawbacks. The process for producing the solid oral anticariogenic composition shall use per se known means, and it shall be possible to perform it in a simple and inexpensive way.

The object of the invention is achieved in a surprisingly simple manner by a solid oral anticariogenic composition in the form of a sucking tablet for cleaning the oral cavity and the teeth which contains from 65 to 95% by weight of isomalt, from 1 to 25% by weight of carbonates, from 0.1 to 5% by weight of citrates, and from 0.1 to 5% by weight of phosphates, in addition to conventional adjuvants, flavors and artificial sweeteners.

Isomalt (E 953, also called Palatinit®), which spares the teeth, is used as a carrier in an amount of preferably from 80 to 90% by weight. The disaccharid alcohol isomalt can be used instead of saccharose or sugar substitutes in almost all foods with sweet taste; in addition, it has the advantage over sorbitol tol (E 420) to be non-cariogenic and thus to spare the teeth. Due to its substantially insulin-independent metabolization, isomalt is suitable for diabetics.

Carbonates, preferably from 6 to 10% by weight of sodium hydrogencarbonate, citrates, preferably calcium and/or potassium citrate, and phosphates, preferably calcium phosphate, are used as acid-binding substances. In addition, these substances have the advantage of being subject to evaluation under food law. According to the German Zusatzstoff-Zulassungsverordnung (food additive approval regulation), these substances fall under the generally approved food additives (see German Zusatzstoff-Verkehrsverordnung (food additive trade regulation), list 6 and list 10). Although the sucking tablet according to the invention is a cosmetic, the acid-binding substances are subject to evaluation under food law, in contrast to urea-containing preparations (for example, according to EP-B-0 222 846).

The basic salt mixture of carbonates, citrates and phosphates according to the invention neutralizes the acids formed from foods and thus protects the teeth from caries.

Menthol and/or peppermint flavor and/or dental flavor, for example, may be used as flavors. The number of flavoring agents which may be used is virtually unlimited. They confer a fresh taste to the sucking tablet.

Sodium cyclamate and/or saccharin are preferably employed as artificial sweeteners.

Magnesium stearate is employed as an adjuvant or emulsifier.

As compared to chewing gums known from the prior art, the sucking tablet according to the invention has the advantage that it is slowly dissolved in the mouth whereas a chewed chewing gum loses its flavor after some time and is then spat out in most cases (environmental pollution!). In addition, the acceptance of a sucking tablet is essentially higher than that of a chewing gum, especially with the older generation.

The preparation of the sucking tablet according to the invention is relatively simple and is described with the designation "direct pressing" in the pharmaceutical field.

In the following Example, the composition according to the invention and the process for producing it are illustrated in more detail:

EXAMPLE

The proportion of ingredients (based on 100 kg) of the composition according to the invention is as follows:

| | |
|---|---|
| isomalt (E 953) | 86.8 kg |
| sodium hydrogen carbonate | 8.0 kg |
| calcium citrate | 0.67 kg |
| potassium citrate | 0.67 kg |
| calcium phosphate | 0.67 kg |
| peppermint flavor, menthol, dental flavor, magnesium stearate; sodium cyclamate, saccharin as artificial sweeteners | 3.19 kg |

The above mentioned powdery ingredients are selected with such properties as to be suitable for direct pressing. This usually means that they have grain diameters within a range of from 100 and 400 μm.

The menthol is then dissolved in the dental flavor and sprayed onto the pressing compound at the end of mixing. Saccharin and sodium cyclamate are premixed in a suitable mixer. Calcium phosphate is added to this mixture. The resulting mixture is mixed with calcium and potassium citrates. Thereafter, magnesium stearate and the peppermint flavor are added, followed by sodium hydrogencarbonate and finally isomalt, incrementally.

The solution of the liquid dental flavor with menthol is applied to this mixture with a suitable spraying system, as mentioned above. Thereafter, the mixture is mixed in a suitable commercial powder mixer and immediately placed on a pharmaceutically usual tablet press (rotary pelleting machine) for direct tabletting, and pressed into appropriate sucking tablets. The hardness of the sucking tablets must be such that they withstand the subsequent automated filling into a suitable container (for example, a tin can) without being damaged.

The sucking tablet is particularly effective if one to three sucking tablets, as needed, are slowly dissolved in the mouth after every meal, which is best done in the cheek pouch.

What is claimed is:

1. A solid oral anticariogenic composition for cleaning the oral cavity and the teeth, characterized by containing from 65 to 95% by weight of isomalt;

from 1 to 25% by weight of carbonates;

from 0.1 to 5% by weight of citrates; and from 0.1 to 5% by weight of phosphates, in addition to conventional adjuvants, flavors and artificial sweeteners.

2. The composition according to claim 1, characterized in that said carbonate is sodium hydrogencarbonate.

3. The composition according to claim 1, characterized in that calcium and/or potassium citrates are employed as said citrates.

4. The composition according to claim 1, characterized in that calcium phosphate is employed as said phosphate.

5. The composition according to claim 1, characterized in that menthol and/or peppermint flavor and/or dental flavor are used as flavors.

6. The composition according to claim 1, characterized in that sodium cyclamate and/or saccharin is employed as an artificial sweetener.

7. The composition according to claim 1, characterized in that magnesium stearate is employed as an adjuvant.

8. The composition according to claim 1, characterized in that its content of isomalt is from 80 to 90% by weight.

9. The composition according to claim 1, characterized in that its content of carbonate is from 6 to 10% by weight.

10. The composition according to claim 1, characterized by being in the form of a sucking tablet.

11. A process for producing a composition according to claim 1, characterized in that a pressable mass is prepared by stepwise mixing of the individual ingredients in a suitable mixer without a thermal load and without using pelleting aids.

12. A solid anticariogenic composition for cleaning the oral cavity comprising, in the absence of sorbitol:
    a) 65–95% by weight isomalt;
    b) 1–25% by weight carbonate;
    c) 0.1–5% citrate;
    d) 0.1–5% phosphate; and
    e) conventional adjuvants, flavors, and artificial sweeteners.

13. The composition of claim 12 in the form of a sucking tablet.

14. The composition of claim 13, wherein the artificial sweetener is sodium cyclamate, saccharin, or a combination thereof, and wherein the adjuvant comprises magnesium stearate.

15. The composition of claim 13, wherein the citrate is calcium citrate, potassium citrate, or a combination thereof.

16. The composition of claim 13, wherein the phosphate is calcium phosphate, and wherein the carbonate is hydrogencarbonate.

17. The composition of claim 12, wherein the artificial sweetener is sodium cyclamate, saccharin, or a combination thereof, and wherein the adjuvant comprises magnesium stearate.

18. The composition of claim 12, wherein the citrate is calcium citrate, potassium citrate, or a combination thereof.

19. The composition of claim 12, wherein the phosphate is calcium phosphate, and wherein the carbonate is hydrogencarbonate.

* * * * *